United States Patent [19]

Bisacchi et al.

[11] Patent Number: 5,064,961
[45] Date of Patent: Nov. 12, 1991

[54] PROCESS FOR PREPARING AN OPTICALLY ACTIVE CYCLOBUTANE NUCLEOSIDE

[75] Inventors: Gregory S. Bisacchi, Titusville; Toomas Mitt, Plainsboro, both of N.J.

[73] Assignee: E. R. Squibb & Sons, Inc., Princeton, N.J.

[21] Appl. No.: 451,664

[22] Filed: Dec. 18, 1989

[51] Int. Cl.$^5$ .............................. C07D 473/18
[52] U.S. Cl. ................... 544/276; 556/436; 560/39; 560/40; 560/173; 564/152; 564/158
[58] Field of Search .......................... 544/276

[56] References Cited

U.S. PATENT DOCUMENTS 4,855,466  8/1989  Zahler et al. .............. 549/546
4,918,075  4/1990  Zahler et al. .............. 514/262

FOREIGN PATENT DOCUMENTS 0335355  10/1989  European Pat. Off. .
358154   3/1990   European Pat. Off. .
366059   5/1990   European Pat. Off. .

OTHER PUBLICATIONS

Ishikawa et al., "Enantio and Diastereo—selective Synthesis . . . ", J. Chem Soc., Chem Commun, 1989, pp. 1919–1921.
Norbeck et al., "Cyclobut A and Cyclobut G . . . ", J. Med. Chem., vol. 33, pp. 1281–1285 (1990).
W. Slusarchyk, et al. SQ 33,054: A Potent Member of a New Class of Nucleoside—Analog Antivirals—Abstract No. 1330—XXIX Interscience on Antimicrobial Agents & Chemo., 9/17-20/89, Houston, TX.
W. Slusarchyk, et al. Synthesis of SQ 33,054, A Novel Cyclobutane Nucleoside with Potent Antiviral Activity; Tetrahedron Letters, vol. 30, p. 6453 (1989).
M. Honjo, et al., Synthesis of the Carbocyclic Analogue of Oxetanocin A$^1$, Chem. Pharm. Bull. 37(5) 14-1-3–1415 (1989).
Y. Hayashi, et al.; Asymmetric [2+2] Cycloaddition Reaction Catalyzed by a Chiral Titanium Reagent, Chemistry Letters, p. 793–796 (1989).

Primary Examiner—Diana G. Rivers
Attorney, Agent, or Firm—Stephen B. Davis

[57] ABSTRACT

A process for the preparation of the optically active compound [IR-(1α, 2β, 3α)]-2-amino-9-[2,3-bis(hydroxymethyl)cyclobutyl]-6H-purin-6-one, represented by the formula:

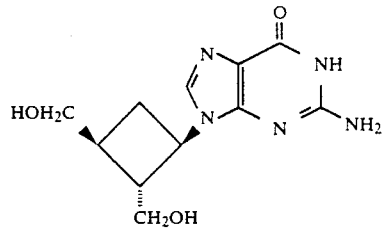

and novel intermediates are described.

14 Claims, No Drawings

PROCESS FOR PREPARING AN OPTICALLY ACTIVE CYCLOBUTANE NUCLEOSIDE

BRIEF DESCRIPTION OF THE INVENTION

The present invention relates to the optically active compound [1R-(1α,2β,3α)]-2-amino-9-[2,3-bis(hydroxymethyl)cyclobutyl]-1,9-dihydro-6H-purin-6-one, represented by formula 1 and to a process for the preparation thereof.

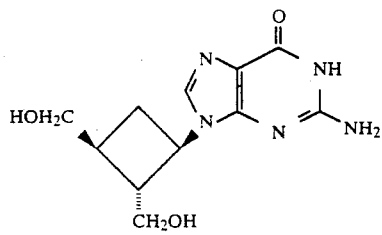

The invention relates to novel intermediates in the above process and to a process for preparing these intermediates.

Compound 1 as a 1:1 mixture with its optical antipode (i.e., the racemic mixture) is an antiviral agent with activity against herpes simplex virus types 1 and 2, varicella zoster virus, human cytomegalovirus, vaccinia virus, murine leukemia virus, and human immunodeficiency virus; and are believed to be active against a variety of other DNA viruses and retroviruses. Antiviral activity is also exhibited by the single enantiomer, compound 1, and its pharmaceutically acceptable salts. Compound 1 as a 1:1 mixture with its optical antipode has been prepared by methods described in European patent application 335,355 published on Oct. 4, 1989.

DETAILED DESCRIPTION OF THE INVENTION

The process of the present invention is shown in the reaction scheme below:

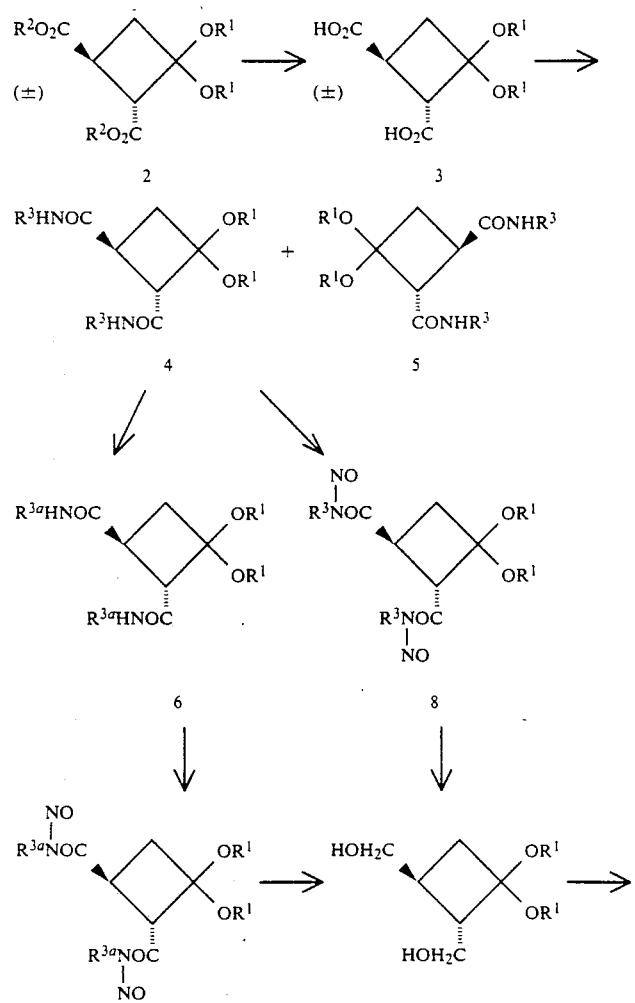

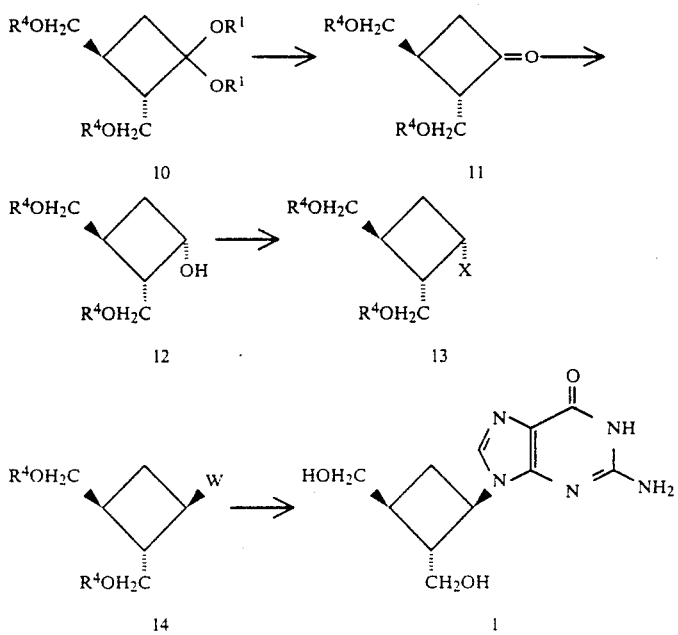

wherein $R^1$ and $R^2$ are lower alkyl, $R^3$ is an alkyl or substituted alkyl group derived from a chiral primary amine of the formula $R^3NH_2$, $R^{3a}$ is a suitably protected form of $R^3$, $R^4$ is a protecting group, X is a leaving group, and W is a 9-guanyl residue or a suitably protected form of a 9-guanyl residue. Compounds 2 and 3 are each racemic mixtures. The relative stereochemistry of the two $R^2O_2C$ groups in compound 2 is trans and the relative stereochemistry of the two $HO_2C$ groups in compound 3 is also trans. Compound 1 and compounds 4 through 14 are chiral compounds, and their absolute stereochemistry is as pictured in the figures of the above reaction schemes.

The term "lower alkyl" refers to both straight and branched chain groups which contain from 1 to 5 carbons. Those groups having 1 to 2 carbons are preferred. The term "alkyl" refers to both straight and branched chain groups. The groups having 1 to 10 carbons are preferred. The term "substituted alkyl" refers to alkyl groups having one or more substituents. Examples of substituents include hydroxy, alkoxy, alkoxycarbonyl, phenyl, hydroxyphenyl, dihydroxyphenyl and nitrophenyl. Preferred substituents are hydroxy and phenyl. When $R^3$ is substituted with hydroxy, $R^3$ should be protected with a suitable hydroxy protecting group to give $R^{3a}$. Exemplary protecting groups are hindered silyl groups such as t-butyldimethylsilyl, t-butyldiphenylsilyl, triisopropylsilyl and the like; acyl groups such as acetyl; aroyl groups such as benzoyl; the triphenylmethyl (trityl) group or a lower alkoxy substituted triphenylmethyl group such as 4′-methoxyphenyldiphenylmethyl. Preferred protecting groups are t-butyldimethylsilyl and acetyl. The protecting group $R^4$ may be a hindered silyl group (such as t-butyldiphenylsilyl or triisopropylsilyl), an acyl group (such as acetyl), an aroyl group (such as benzoyl), a benzyl group or a substituted benzyl group (such as p-methoxybenzyl). The leaving group X may be an alkanesulfonyloxy group (such as methanesulfonyloxy(mesyl)), a substituted alkanesulfonyloxy group (such as trifluoromethanesulfonyloxy (triflyl)), or an arene- or substituted arenesulfonyloxy group (such as p-toluenesulfonyloxy group (tosyl) or p-nitrobenzenesulfonyloxy group (nosyl)). The group W includes the 2-amino-6-benzyloxypurin-9-yl, 2-amino-6-methoxyethoxypurin-9-yl, 2-amino-6-chloropurin-9-yl, and 2-acetamido-6-hydroxypurin-9-yl residues as suitably protected forms of the 9-guanyl residue. The 2-amino-6-benzyloxypurin-9-yl and 2-amino-6-methoxyethoxypurin-9-yl residues are preferred as protected forms of the group W.

The racemic compound of formula 2 wherein $R^1$ and $R^2$ are lower alkyl can be prepared by reacting ketene di(lower alkyl)acetal with di(lower alkyl)fumarate (see K. C. Brannock et al., *J. Org. Chem.*, 29, 940 (1964)). Preferentially $R^1$ and $R^2$ are methyl or ethyl. For example, ketene diethyl acetal is reacted with diethyl-fumarate either neat or in an appropriate solvent such as acetonitrile, t-butanol, or the like, preferably t-butanol. The mixture is stirred for about 4 to 10 days, preferably for about 6 to 8 days, at a temperature of about 70° C. to 100° C., preferably of about 80° C. to 90° C. The resultant compound 2 can be isolated by chromatography or distillation.

Di(lower alkyl)fumarates are either commercially available (e.g., Aldrich Chemical Co.) or can be readily prepared by methods known in the art. Ketene di(lower alkyl)acetals are either commercially available (e.g., Wiley Organics Inc.) or can be readily prepared by known methods (see e.g., *Organic Syntheses, Collective Volume III*, p. 506; *J. Amer. Chem. Soc.*, 62, 964 (1940)).

The racemic compound of formula 3 is prepared by treatment of the compound of formula 2 with alkali, preferably potassium hydroxide, in aqueous or mixed aqueous-organic solvent solutions, for example, water-dioxane, water-tetrahydrofuran, water-tetrahydrofuran-methanol and the like, preferably water-tetrahydrofuranmethanol. The mixture is stirred for 1 to 5 days, preferably for 2 to 3 days at a temperature of 10° C. to 50° C., preferably of 20° C. to 30° C. The reaction mixture is diluted with water, acidified to about pH 2.5 with aqueous acid and extracted with an organic solvent such as dichloromethane, ethyl acetate, and the like, followed by concentration of the organic solvent.

The diastereomeric mixture of compounds 4 and 5 is prepared by treatment of compound 3 with a chiral primary amine ($R^3NH_2$) in the presence of a coupling agent such as 1,3-dicyclohexylcarbodiimide, 1-(3-dimethylaminopropyl)-3-ethylcarbodiimide hydrochloride, and the like, in a solvent such as methylene chloride or tetrahydrofuran. To this reaction mixture, additional reaction components such as 1-hydroxybenzotriazole, or 1-hydroxybenzotriazole plus N-methylmorpholine, may optionally be added. The mixture is stirred at about 0° C. to 50° C., preferably at about 20° C. to 30° C. for 1 to 48 hours, preferably for 10 to 18 hours. Water is added to the reaction mixture, and the mixture of compounds 4 and 5 is isolated by extraction.

Examples of suitable chiral primary amines, $R^3NH_2$, include chiral alkyl amines such as (+)- or (−)-2-aminobutane and (+)- or (−)-2-aminoheptane; chiral hydroxy-substituted alkylamines such as (+)- or (−)-2-amino-1-butanol, (+)- or (−)-2-amino-1-propanol, (+)- or (−)-2-amino-3-methyl-1-butanol, (+)- or (−)-leucinol, and (+)-isoleucinol; chiral phenyl or naphthyl-substituted alkyl amines such as (+)- or (−)-α-methylbenzylamine, (+)- or (−)-α-(1-naphthyl)ethylamine, and (+)- or (−)-α-(2-naphthyl)ethylamine; chiral alkylamines substituted with both hydroxy and phenyl such as (+)- or (−)-2-phenylglycinol, (+)- or (−)-threo-2-amino-1-phenyl-1,3-propanediol, (+)- or (−)-norephedrine, (+)- or (−)-2-amino-3-phenyl-1-propanol, and (+)- or (−)-2-amino-1,2-diphenylethanol; and other substituted alkylamines such as (+)- or (−)-α-methyl-p-nitrobenzylamine, (+)- or (−)-threo-2-amino-1-(4-nitrophenyl)-1,3-propanediol, (+)- or (−)-norepinephrine, (+)-dehydroabietylamine, (+)-2-amino-3-methoxy-1-phenylpropanol, L-tyrosinol, and lower alkyl esters of α-amino acids such as (+)- or (−)-alanine, (+)- or (−)-valine, (+)- or (−) leucine, (+)- or (−)-isoleucine, (+)- or (−)-phenylalanine, (+)- or (−)-tyrosine, (+)- or (−)-serine, and (+)- or (−)-threonine. Preferred chiral alkylamines include those substituted with both hydroxy and phenyl groups; most preferred is (−)-2-phenylglycinol.

Compounds 4 and 5 may be separated by chromatography (e.g. on silica gel), or by crystallization from various solvents and solvent mixtures such as methylene chloride, chloroform, ether, ether-methanol, water, and the like. When the chiral amine $R^3NH_2$ is (−)-2-phenylglycinol, the resultant compound 4 is separated preferably by crystallization from methylene chloride.

When the group $R^3$ of compound 4 is substituted with a hydroxy group, the hydroxy is protected to afford compound 6, wherein the group $R^{3a}$ is the protected form of $R^3$. A compound of formula 6 wherein the hydroxy group of $R^3$ has been protected with a hindered silyl group such as t-butyldimethylsilyl, t-butyldiphenylsilyl, or triisopropylsilyl is prepared by treating the compound of formula 4 with the appropriate silyl reagent such as the corresponding tri(hydrocarbon)silyl chloride. Compound 4 is reacted with the silyl reagent in a solvent such as dimethylformamide, tetrahydrofuran, acetonitrile, and the like, preferably dimethylformamide, at −10° C. to 30° C., preferably at 0° C. to 20° C. for ¼ hour to 2 hours, preferably for ½ hour to 1 hour. The reaction is run in the presence of a base such as triethylamine, pyridine, or imidazole, preferably imidazole. The compound of formula 6 is extracted and optionally purified by, e.g. chromatography on silica gel.

The compound of formula 6 wherein the hydroxy group has been protected with an acyl or aroyl group such as acetyl or benzoyl is prepared by treating the compound of formula 4 with the corresponding acyl or aroyl chloride or with the corresponding acyl or aroyl anhydride in a solvent such a pyridine or tetrahydrofuran. When tetrahydrofuran is used as solvent, a base such as triethylamine is added.

A compound of formula 6 wherein the hydroxy group has been protected with a trityl or a lower alkoxy substituted trityl group is prepared by treating the compound of formula 4 with trityl chloride or the lower alkoxy substituted trityl chloride in a solvent such as pyridine.

A compound of formula 7 is prepared by reacting a compound of formula 6 with a suitable nitrosating agent such as nitrosyl chloride, nitronium tetrafluoroborate, nitrogen tetroxide ($N_2O_4$), and the like, preferably nitrogen tetroxide. (See e.g., E. H. White, *J. Amer. Chem. Soc.*, 77 6008 (1955) and J. Vilarrasa, *J. Org. Chem.*, 54, 3209 (1989) for a discussion of various nitrosating agents). For example, a compound of formula 6 is treated with nitrogen tetroxide in a solvent such as carbon tetrachloride, methylene chloride and the like, preferably carbon tetrachloride, in the presence of a base such as sodium acetate, pyridine, and the like, preferably sodium acetate. The reaction mixture is stirred for ¼ hour to 4 hours, preferably ½ hour to 1½ hours at −10° C. to 20° C., preferably at −5° C. to 10° C. The mixture is poured into ice water and extracted.

A compound of formula 8 is prepared from a compound of formula 4 when the group $R^3$ does not contain a hydroxy substituent. The preparation of a compound of formula 8 from a compound of formula 4 is accomplished in the same manner as described for the preparation of a compound of formula 7 from a compound of formula 6.

A compound of formula 9 is prepared by treating a compound of formula 7 or a compound of formula 8 with a suitable reducing agent such as lithium aluminum hydride, sodium borohydride, lithium borohydride and the like, preferably lithium borohydride. For example, a compound of formula 7 or a compound of formula 8 is treated with lithium borohydride in a solvent such as tetrahydrofuran, ether, dimethoxyethane (glyme) and the like, preferably tetrahydrofuran, at −20° C. to 20° C., preferably at −10° C. to 10° C. for ¼ hour to 2 hours, preferably ½ hour to 1 hour. The reaction mixture is quenched with water and the product is extracted and purified by e.g. chromatography.

A compound of formula 10 wherein $R^4$ is a suitable protecting group is prepared by reacting a compound of formula 9 with the corresponding protecting group precursor. Suitable protecting groups $R^4$ include hindered silyl groups (such as t-butyldiphenylsilyl or triisopropylsilyl), benzyl or substituted benzyl groups (such as p-methoxybenzyl), aroyl groups (such as benzoyl) and acyl (such as acetyl). Benzyl and benzoyl are preferred for $R^4$. A compound of formula 10 wherein $R^4$ is a hindered silyl group is prepared by treating a compound of formula 9 with the appropriate silyl reagent e.g., the corresponding silyl chloride, using reaction conditions described previously. A compound of formula 10 wherein $R^4$ is a benzyl or substituted benzyl is prepared by treating a compound of formula 9 with a benzyl halide or a substituted benzyl halide in a solvent such as tetrahydrofuran or dimethylformamide in the presence of a suitable base such as sodium hydride. A compound of formula 10 wherein $R^4$ is an acyl or aroyl group is prepared by treating a compound of formula 9 with the corresponding acyl- or aroyl-anhydride or halide, preferably benzoyl chloride, in a solvent such as pyridine or tetrahydrofuran/triethylamine, preferably pyridine. The benzoylation reaction is carried out at $-10°$ C. to 20° C., preferably at $-5°$ C. to 5° C., for $\frac{1}{4}$ hour to 2 hours, preferably for $\frac{1}{2}$ hour to $1\frac{1}{2}$ hours. Water is added to the reaction mixture, the mixture is stirred overnight, and the product is extracted and optionally purified e.g. by chromatography.

A compound of formula 11 is prepared by treatment of a compound of formula 10 with an acid catalyst such as sulfuric acid, hydrochloric acid, p-toluenesulfonic acid, and the like, preferably sulfuric acid, in a solvent or solvent mixture such as water, water-acetonitrile, water-dioxane, acetone, and the like, preferably water-acetonitrile. The reaction mixture is stirred at 0° C. to 60° C., preferably at 15° C. to 30° C. for $\frac{1}{2}$ hour to 2 days, preferably for 2 hours to 8 hours. The reaction mixture is neutralized, and the product is extracted and optionally purified by e.g. chromatography.

A compound of formula 12 is prepared by reaction of a compound of formula 11 with a suitable reducing agent. Reducing agents may include hindered hydride reagents such as lithium tri-sec-butylborohydride, lithium trisiamylborohydride, diisobutylaluminum hydride and the like, preferably lithium trisiamylborohydride and hindered borane reducing agents such as dicyclohexylborane, disiamylborane, and the like. The reaction is run in a solvent such as ether, tetrahydrofuran, glyme, and the like, preferably tetrahydrofuran. When a hindered borohydride reducing agent is employed the reaction mixture is stirred at $-90°$ C. to $-60°$ C., preferably $-80°$ C. to $-70°$ C. for 5 minutes to 1 hour, preferably for $\frac{1}{4}$ hour to $\frac{1}{2}$ hour and the mixture is allowed to warm to 0° C. to 30° C., preferably 20° C. to 25° C. The reaction is worked up with aqueous sodium bicarbonate-hydrogen peroxide and the product is isolated by extraction and optionally purified by e.g. chromatography.

A compound of formula 13 wherein X is a leaving group such as an alkanesulfonyloxy group (e.g., mesyl), a substituted alkanesulfonyloxy group (e.g., triflyl), or an arene- or substituted arenesulfonyloxy group (e.g., tosyl or nosyl), may be prepared by treatment of a compound of formula 12 with the appropriate sulfonylating reagent such as the corresponding sulfonic anhydride or sulfonyl chloride, preferably tosyl chloride, in a solvent such as pyridine, tetrahydrofuran, methylene chloride, and the like, preferably pyridine. When non-basic solvents such as tetrahydrofuran, methylene chloride and the like are employed for the reaction, a base such as triethylamine is added to the mixture. Depending on the solvent and the sulfonating reagent, the reaction mixture is stirred at 0° C. to 60° C., for 1 hour to 48 hours. For example, a mixture of a compound of formula 12 and tosyl chloride in pyridine is stirred at 60° C. overnight. The product is isolated by extraction and optionally purified by, e.g., chromatography.

A compound of formula 14, wherein W is a 9-guanyl residue or a protected form of the 9-guanyl residue is prepared by reaction of a compound of formula 13 with guanine or the corresponding protected guanine. Protected forms of guanine include 2-amino-6-benzyloxypurine, 2-amino-6-methoxyethoxypurine, 2-amino-6-chloropurine, and 2-acetamido-6-hydroxypurine. Preferred protected forms of guanine are 2-amino-6-benzyloxypurine and 2-amino-6-methoxyethoxypurine. A mixture of the compound of formula 13 and guanine or a protected guanine, and a base such as potassium carbonate, sodium hydride, and the like, preferably potassium carbonate, is stirred in a solvent such as dimethylformamide, dimethylsulfoxide, sulfolane, and the like, preferably dimethylformamide. The mixture is heated to 40° C. to 150° C., preferably 100° C. to 120° C. for 4 hours to 48 hours, preferably for 12 hours to 24 hours. Crown ethers such as 18-crown-6 when the base is potassium carbonate, or 15-crown-5 when the base is sodium hydride, may optionally be added to the reaction mixture. The product is purified e.g. by chromatography.

The compound of formula 1 is prepared by deprotecting a compound of formula 14. For a compound of formula 14 wherein W is a 9-guanyl residue, the protecting groups $R^4$ are removed. For a compound of formula 14 wherein W is a protected 9-guanyl residue, the protecting groups $R^4$ may be removed first, followed by deprotection of the 9-guanyl residue, or the 9-guanyl residue may be deprotected first followed by removal of the $R^4$ groups, or all protecting groups may be removed simultaneously. The method of deprotection depends on the particular protecting groups employed. For a compound of formula 14 wherein W is a 9-guanyl residue and $R^4$ is a hindered silyl group, $R^4$ is removed by treatment with a fluoride reagent such as tetra-n-butylammonium fluoride, pyridinium fluoride, and the like or by hydrolysis with acid or base. (See T. W. Green, *Protective Groups in Organic Synthesis*, Wiley-Interscience, 1981, for a detailed discussion of such deprotection procedures). For a compound of formula 14 wherein W is a 9-guanyl residue and $R^4$ is a benzyl or substituted benzyl group, $R^4$ is removed under reductive conditions such as by treatment with dissolving metal reagent (e.g. sodium in liquid ammonia), by hydrogenolysis (e.g. hydrogen gas in the presence of a catalyst such as palladium on carbon, or cyclohexene in the presence of a catalyst such as palladium hydroxide on carbon), or by treatment with a reagent such as boron trichloride. For a compound of formula 14 wherein W is a 9-guanyl residue and $R^4$ is an acyl group such as acetyl or an aroyl group such as benzoyl, $R^4$ is removed by basic hydrolysis, for example, by treatment with an aqueous metal hydroxide such as potassium hydroxide, or by treatment with a metal alkoxide in an alcohol solvent such as sodium methoxide in methanol.

For a compound of formula 14 wherein W is a 6-benzyloxy-2-aminopurin-9-yl residue and $R^4$ is a hindered silyl group, $R^4$ may be removed first using a fluoride reagent and the W group may then be deprotected by acidic hydrolysis, by reduction either by a dissolving metal agent or by hydrogenolysis, or by treatment with a reagent such as boron trichloride. Alternatively, the W group may be first deprotected e.g. by reduction with a dissolving metal reagent or by hydrogenolysis, followed by removal of the silyl $R^4$ group by treatment with a fluoride reagent. Alternatively, simultaneous deprotection of both the W and $R^4$ groups can be accomplished by acidic hydrolysis. For a compound of formula 14 wherein W is a 6-benzyloxy-2-aminopurin-9-yl residue and $R^4$ is a benzyl or substituted benzyl group, deprotection of the W group can be accomplished first by acidic hydrolysis, followed by reductive removal of the $R^4$ groups. Alternatively, all of the protecting groups can be removed simultaneously under, for example, reductive conditions or by treatment with a reagent such as boron trichloride. For a compound of formula 14 wherein W is a 6-benzyloxy-2-aminopurin-9-yl residue and $R^4$ is an acyl group such as acetyl or an aroyl group such as benzoyl, the aroyl groups may be removed first by basic hydrolysis, followed by deprotection of the W group e.g. by reduction, by acidic hydrolysis, or by treatment with a reagent such as boron trichloride. For example, for a compound of formula 14 wherein W is a 6-benzyloxy-2-aminopurin-9-yl residue and $R^4$ is benzoyl, the benzoyl groups are preferentially removed first by treatment with a solution of sodium methoxide in methanol at 20° C. to 60° C., preferably at 30° C. to 50° C. for ¼ hour to 6 hours preferably for ½ hour to 2 hours. The mixture is neutralized, concentrated and treated with hydrochloric acid in water-methanol at 30° C. to 60° C., preferably at 45° C. to 55° C. for ½ hour to 12 hours, preferably for 1 hour to 3 hours. The reaction mixture is neutralized, and the product, compound 1 is purified by e.g. chromatography.

For a compound of formula 14 wherein W is a 2-amino-6-methoxyethoxypurin-9-yl residue and $R^4$ is a hindered silyl group, the silyl group may first be removed with a fluoride reagent followed by deprotection of the W residue by acidic hydrolysis. Alternatively, all protecting groups may be removed simultaneously by acidic hydrolysis. For a compound of formula 14 wherein W is a 2-amino-6-methoxyethoxypurin-9-yl residue and $R^4$ is a benzyl or substituted benzyl group, the W residue may be first deprotected by acidic hydrolysis, followed by removal of the $R^4$ groups under reductive conditions (e.g. with a dissolving metal reagent or by hydrogenolysis) or by treatment with a reagent such as boron trichloride. For a compound of formula 14 wherein W is a 2-amino-6-methoxyethoxypurin-9-yl residue and $R^4$ is an acyl group such as acetyl or an aroyl group such as a benzoyl, the $R^4$ groups may be removed by basic hydrolysis, followed by deprotection of the W residue by acidic hydrolysis. Alternatively, all of the protecting groups may be removed simultaneously by acidic hydrolysis.

For a compound of formula 14 wherein W is a 2-amino-6-chloropurin-9-yl residue and $R^4$ is a hindered silyl group, the silyl group may first be removed with a fluoride reagent followed by deprotection of the W residue by acidic hydrolysis. Alternatively, all protecting groups may be removed simultaneously by vigorous acidic hydrolysis. For a compound of formula 14 wherein W is a 2-amino-6-chloropyrin-9-yl residue and $R^4$ is a benzyl or substituted benzyl group, the W residue may be first deprotected by acidic hydrolysis, followed by removal of the $R^4$ groups under reductive conditions or by treatment with a reagent such as boron trichloride or trimethylsilyl iodide. For a compound of formula 14 wherein W is a 2-amino-6-chloropurin-9-yl residue and $R^4$ is an aroyl group such as benzoyl, the W residue may be first deprotected by acidic hydrolysis, followed by removal of the $R^4$ groups by basic hydrolysis. Alternatively, all of the protecting groups may be removed simultaneously by aqueous basic hydrolysis.

For a compound of formula 14 wherein W is a 2-acylamino-6-hydroxypurin-9-yl residue and $R^4$ is a hindered silyl group, the silyl group may first be removed with a fluoride reagent followed by deprotection of the W residue by basic hydrolysis. Alternatively, all protecting groups may be removed simultaneously be aqueous basic hydrolysis. For a compound of formula 14 wherein W is a 2-acylamino-6-hydroxypurin-9-yl residue and $R^4$ is a benzyl or substituted benzyl group, the W residue may first be deprotected by basic or acidic hydrolysis, followed by removal of the $R^4$ group under reductive conditions (e.g., with a dissolving metal reagent or by hydrogenolysis) or by treatment with a reagent such as boron trichloride. For a compound of formula 14 wherein W is a 2-acylamino-6-hydroxypurin-9-yl residue and $R^4$ is an acyl group such as acetyl or an aroyl group such as a benzoyl all of the protecting groups may be removed simultaneously by basic or acidic hydrolysis.

The following examples are specific embodiments of the invention.

EXAMPLE 1

[1R-(1α,2β,3α)]-2-Amino-9-[2,3-bis-(hydroxymethyl)-cyclobutyl]-1,9-dihydro-6H-purin-6-one

EXAMPLE 1a trans-3,3-Diethoxy-1,2-cyclobutanedicarboxylic acid, diethyl ester (racemic mixture)

A mixture of diethylketene acetal (38.35 g) and diethylfumarate (53.5 ml) in t-butanol (90 ml) was heated at 84° C. for 72 hours. Distillation of the reaction mixture (113°-125° C., 0.6-1.6 mm Hg) afforded 50.4 g of product.

EXAMPLE 1b trans-3,3-Diethoxy-1,2-cyclobutanedicarboxylic acid (racemic mixture)

A solution of tras-3,3-diethoxy-1,2-cyclobutanedicarboxylic acid, diethyl ester (100 g) in 1400 ml of tetrahydrofuran under argon was treated with 1400 ml of methanol and 1400 ml of 1N potassium hydroxide solution. The resulting mixture was allowed to stand for 3 days at room temperature and then was evaporated in vacuo to an aqueous solution. The pH was adjusted to 2.3 with 3N hydrochloric acid and the solution was saturated with sodium chloride. The resulting suspension was extracted with ethyl acetate (3×1000 ml). The combined extracts were washed with 250 ml of water and 250 ml of brine, dried over sodium sulfate, and evaporated to afford the product as solid, 78.8 g, m.p. 118°-120° C.

EXAMPLE 1c

[1S-[1α(S*), 2β(S*)]]-3,3-Diethoxy-N,N'-bis(2-hydroxy-1-phenylethyl) -1,2-cyclobutanedicarboxyamide A suspension of 60.0 g of trans-3,3-diethoxy-1,2-cyclobutanedicarboxylic acid in 500 ml of methylene chloride under argon was treated with 92.4 g of R-(−)-2-phenylglycinol. The resulting solution was cooled in an ice bath and treated with 120 g of 1,3-dicyclohexylcarbodiimide. The mixture was stirred overnight at ambient temperature and then was diluted with 1500 ml of diethyl ether and filtered. The filtrate was washed with 10% sodium bisulfate (twice), saturated sodium bicarbonate (twice) and brine (twice). The organic phase was dried over sodium sulfate and evaporated to a semi-solid which was chromatographed on a column of silica gel (2.5 L), eluting with ethyl acetate-hexane followed by methanol-ethyl acetate. Combination of appropriate fractions gave a mixture of the two isomers,

[1S-[1α(S*),2β(S*)]]-3,3-diethoxy-N,N'-bis (2-hydroxy-1-phenylethyl)-1,2-cyclobutanedicarboxamide and [1R-[1α(R*),2β(R*)]]-3,3-diethoxy-N,N'-bis -(2-hydroxy-1-phenylethyl)-1,2-cyclobutanedicarboxamide as a foam (88.7 g). This mixture was dissolved almost completely in 600 ml of methylene chloride with heating. This solution was chilled at 5° C. for 4 hours and the resulting solid was filtered and washed with 150 ml of cold methylene chloride. Drying in vacuo gave 31 g of solid. Concentration of the mother liquors and chilling at −30° C. for 12 hours gave a second crop of solid. Similar solid from several preparations (98.1 g) was heated with 2500 ml of methylene chloride until nearly completely dissolved. The solution was chilled at 5° C. overnight and filtered, and the solid was washed with 500 ml of cold methylene chloride. Drying in vacuo gave 83 g of the desired product, which was completely free of the other isomer, [1R-[1α(R*),2β(R*)]]-3,3-diethoxy-N,N'-bis(2-hydroxy-1-phenylethyl) -1,2-cyclobutanedicarboxamide, as judged by HPLC. The mother liquor was concentrated to 150 ml, heated to partially dissolve solids, and then cooled in an ice bath for 1 hour. The resulting solid was filtered and washed with 50 ml of cold methylene chloride and dried in vacuo to give an additional 11.8 g of the product, isomerically pure. An analytical sample was obtained by recrystallization from ethyl acetate, m.p. 128°–129° C., [α]$_D$−16.8° (c=1.00, methanol). The absolute stereochemistry of the product was ascertained by X-ray crystallographic analysis (crystals obtained by recrystallization form water).

EXAMPLE 1d

[1S-[1α(S*),2β(S*)]]-N,N'-Bis[2-[[(1,1-dimethylethyl)dimethylsilyl]oxy]-1-phenylethyl]-3,3-diethoxy-1,2-cyclobutanedicarboxamide A slurry of 23.5 g of [1S-[1α(S*), 2β(S*)]]-3,3-diethoxy-N,N'-bis (2-hydroxy-1-phenylethyl)-1,2-cyclobutanedicarboxamide and 13.6 g of imidazole in 100 ml dry dimethylformamide under nitrogen was cooled to 0° C. and treated with 15.8 g of solid t-butyldimethylsilyl chloride. After stirring at 0° C. for 1.5 hours, the mixture was diluted to 600 ml with ethyl acetate and washed with 3% hydrochloric acid (thrice), water (once), and brine (twice). Drying over sodium sulfate and evaporation gave an oily solid. This was taken up in 50 ml of ethyl acetate and diluted with 200 ml of hexane. The resulting slurry was filtered and the cake was washed with 100 ml of 20% ethyl acetate in hexane. Evaporation of the filtrate in vacuo afforded the product as a clear glass, 33.6 g.

EXAMPLE 1e

[1S-[1α(S*),2β(S*)]]-N,N'-Bis[2-[[(1,1-dimethylethyl)dimethylsilyl]oxy]-1-phenylethyl]-3,3-diethoxy-N,N'-dinitroso-1,2-cyclobutanedicarboxamide A solution of 33.6 g of 1S-[1α(S*), 2β(S*)]]-N,N'-bis[2-[[(1,1-dimethylethyl)dimethylsilyl]oxy]-1-phenylethyl]-3,3-diethoxy-1,2-cyclobutanedicarboxamide in 250 ml of dry carbon tetrachloride was treated with 35 g of fresh anhydrous sodium acetate. The resulting slurry was chilled in an ice bath and treated with stirring over 15 minutes with 75 ml of a 2.76M solution of nitrogen tetroxide in carbon tetrachloride. The resulting yellow mixture was stirred for another 15 minutes at 0° C. and then was poured into a mixture of ice (500 ml), water (200 ml), sodium acetate trihydrate (100 g), and methylene chloride (500 ml). The mixture was shaken for a few minutes and the resulting yellow organic layer was separated and washed with brine. Drying over magnesium sulfate and evaporation in vacuo at <15° C. gave 46.6 g of the product as a thick yellow oil.

EXAMPLE 1f (1S-trans)-3,3-diethoxy-1,2-cyclobutanedimethanol 46.6 g of [1S-[1α(S*),2β(S*)]]-N,N'Bis[2-[[(1,1-dimethylethyl)dimethylsilyl]oxy-1-phenylethyl]-3,3-diethoxy-N,N'-dinitroso -1,2-cyclobutanedicarboxamide, was dissolved in 200 ml of dry tetrahydrofuran and the resulting solution was chilled at 0° C. and cannulated into a 0° C. solution of lithium borohydride in tetrahydrofuran (150 ml of a 2M solution). The addition took 15 minutes after which the cooling bath was removed and the clear orange mixture was allowed to stir at ambient temperature overnight. The resulting nearly colorless solution was chilled in an ice bath while being treated with 25 ml of water dropwise. The resulting slurry was diluted with 500 ml of diethyl ether and water was added to dissolve most of the solid (100 ml). The layers were separated and the aqueous layer was extracted with more ether and finally with ethyl acetate. The organic layers were combined, dried over sodium sulfate, and concentrated to afford 33.8 g of an oil. Chromatography on a column of silica gel eluting with ethyl acetate-hexane followed by ethyl acetate, afforded 8.0 g of the product as a colorless oil. An analytical sample was obtained by semi-preparative HPLC, [α]$_D$−17.3° (c=1.06, chloroform).

EXAMPLE 1g (1S-trans)-3,3-Diethoxy-1,2-cyclobutanedimethanol,-dibenzoate ester (1S-trans)-3,3-Diethoxy-1,2-cyclobutanedimethanol (35.1 g) was dissolved in 250 ml of dry pyridine, cooled to 0° C. under argon, and treated over 0.5 hours with benzoyl chloride (59.7 ml). The cooling bath was removed and the mixture was stirred at ambient temperature for 2.5 hours. The mixture was then cooled to 0° C. and treated over 5 minutes with 125 ml of water. The cooling bath was removed and the mixture was stirred at ambient temperature for 18 hours. The mixture was concentrated in vacuo and the residue was co-distilled with water (×3) and with toluene (×2) in vacuo. The residue was partitioned between ethyl acetate and water. The organic layer was washed with 10% sodium bisulfate (2×250 ml), water (4×250 ml), saturated sodium bicarbonate (2×250 ml), and water (3×250 ml). Drying over sodium sulfate, concentration in vacuo and azetroping with carbon tetrachloride gave 83 g of the title compound as a semi-solid.

EXAMPLE 1h (2S-trans)-2,3-Bis[benzoyloxymethyl]cyclobutanone

The above sample of (1S-trans)-3,3-Diethoxy -1,2-cyclobutanedimethanol, dibenzoate ester (83 g) was dissolved in acetonitrile (1.75 L) under argon and treated with 660 ml of 0.5N sulfuric acid. The mixture was stirred at ambient temperature for 17 hours and then was diluted with 5 L of ethyl acetate. This solution was washed with water (2×1 L), saturated sodium bicarbonate (1 L), water (2×1 L), and brine (1 L). The organic phase was dried over sodium sulfate and evaporated to a white solid in vacuo. Partial dissolution in 400 ml of ether and cooling at −30° C. for 2 hours gave a solid which was filtered, washed with cold ether and dried in air to give 46.4 g of the title compound, m.p. 93°-94° C., $[\alpha]_D = +22.8°$ (c=1.0, CHCl$_3$).

Another 8 g of slightly impure title compound was obtained by evaporation of the filtrate to a solid residue.

EXAMPLE 1i

[1S-(1α,2β,3β)]-3-hydroxy-1,2-cyclobutanedimethanol, 1,2-dibenzoate ester (2S-trans)-2,3-Bis[benzoyloxymethyl]cyclobutanone (33.81 g) in 440 ml of dry tetrahydrofuran at −78° C. under argon was treated with 100 ml of 1M lithium trisiamylborohydride in tetrahydrofuran over 20 minutes. After stirring another 10 at −78° C., the mixture was warmed to room minutes at −78° C., the mixture was warmed to room temperature, and 100 ml of saturated sodium bicarbonate was added over 5 minutes. The resultant mixture was cooled in an ice-acetone bath and treated with 36.5 ml of 30% hydrogen peroxide at a rate so as to maintain the temperature at 25°-30° C. After the addition, the mixture was diluted with 300 ml of water and extracted with 1.1 L of ethyl acetate. The organic phase was washed with water (×3), dried over sodium sulfate, and concentrated to a colorless oil (35 g). The oil was taken up in 100 ml of hexane/ethyl acetate (2/1) and filtered through a 1 L pad of silica gel(K-60), eluting with the same solvent mixture. Evaporation of the pure fractions gave 27 g of pure title compound as a colorless oil. Another 4.4 g of slightly impure material gave 3.4 g of pure title compound after column chromatography in the same solvent mixture.

EXAMPLE 1j

[1S-(1α,2β,3β)]-3[[(4-Methylphenyl)sulfonyl]oxy]-1,2-cyclobutanedimethanol, dibenzoate ester 1S-(1α,2β,3β)]-3-hydroxy-1,2-cyclobutanedimethanol, 1,2-dibenzoate ester (27 g) was dissolved in 110 ml of dry pyridine under argon and treated with p-toluenesulfonyl chloride (16.7 g). The mixture was heated and stirred at 60° for 16 hours, cooled to 40° C. and treated with 2 ml of water. After stirring for 2 hours at 40° C. the mixture was concentrated in vacuo to an oil. After azetroping with 2×150 ml of water in vacuo, the residue was partitioned between water and ethyl acetate. The organic phase was washed with water (×2), saturated sodium bicarbonate (×2), and brine. Drying over sodium sulfate and evaporation in vacuo gave 32.2 g of an oil. Trituration with pentane gave 28.3 g of a solid. Crystallization from ethyl acetate/pentane gave 18.4 g of pure title compound as a solid, m.p. 91°-92° C., $[\alpha]_D = +13.8°$ (c=1.3, CHCl$_3$). Another 4 g of title compound was obtained by chromatography of the mother liquors on silica gel using hexane/ethyl acetate (3/1).

EXAMPLE 1k

[1S-(1α,2β,3α)]-3-[2-Amino-6-(phenylmethoxy) -9H-purin-9-yl]-1,2-cyclobutanedimethanol, dibenzoate ester A mixture of dry 2-amino-6-benzyloxyguanine (13.4 g), [1S-(1α,2β,3β)]-3[[(4-methylphenyl)sulfonyl]oxy]-1,2-cyclobutanedimethanol, dibenzoate ester, (18.33 g), powdered anhydrous potassium carbonate (10.22 g, dried over phosphorus pentoxide in vacuo at 130° C. for 72 hours), and 18-crown-6 (9.8 g) in 495 ml of dry dimethylformamide was stirred and heated at 110° C. under argon for 21 hours. The mixture was cooled to room temperature and filtered, and the filtrate was evaporated in vacuo to an oil which was partitioned between ethyl acetate and water. The organic phase was washed twice with water, dried over sodium sulfate, and evaporated to a foam (24.4 g). Chromatography on silica gel in hexane/ethyl acetate (1/1) gave 10.7 g of the title compound as a foam with $[\alpha]_D = -9.0°$ (c=0.67, CHCl$_3$).

EXAMPLE 1L

[1R-(1α,2β,3β)]-2-Amino-9-[2,3-bis(hydroxymethyl) cyclobutyl]-1,9-dihydro-6H-purin-6-one A solution of [1S-(1α,2β,3α)]-3-[2-amino-6-(phenylmethoxy)-9H -purin-9-yl]-1,2-cyclobutanedimethanol, dibenzoate ester (20.0 g) in 550 ml of methanol under argon was treated with 5 ml of 25% sodium methoxide in methanol and heated at 40° C. for 2 hours. Aqueous hydrochloric acid (3N, 275 ml) was then added to the reaction mixture, and heating was continued at 50° C. for 2 hours. This mixture was concentrated to 100 ml and the solution was transferred to a separatory funnel, with addition of another 100 ml of water. The solution was extracted with ether (3×100 ml) and the pH of the aqueous layer was adjusted to 8.5 with the slow addition of 360 ml of 2N potassium hydroxide. The resulting thick precipitate was filtered and the damp solid was recrystallized by dissolving in 200 ml of hot water, filtering while hot, and chilling at 5° C. overnight. Drying in vacuo over phosphorus pentoxide gave 7.65 g of an impure white solid. Chromatography on 750 ml of CHP-20P resin with gradient elution using acetonitrile and water, concentration of the pertinent product fractions until turbid, and chilling this turbid solution for 1 hour at 0° C. gave crystals which were filtered. Drying in vacuo at room temperature over phosphorus pentoxide gave 6.3 g of the title compound as a white crystalline solid, m.p. >270° C., $[\alpha]_D = -27°$ (c=1.0, DMSO).

What is claimed is:

1. A process for the preparation of the optically active compound [1R-(1α,2β,3α)]-2-amino-9-[2,3-bis(hydroxymethyl) cyclobutyl]-1,9-dihydro-6H-purin -6-one, represented by the formula

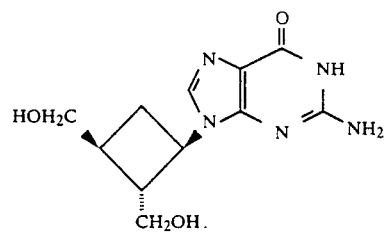

which comprises
(1) reacting a racemic compound of the formula

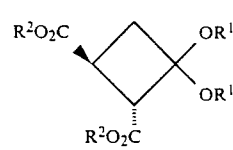

2 wherein R$^1$ and R$^2$ are lower alkyl with alkali to yield the racemic compound of the formula

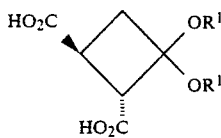                                          3 wherein $R^1$ is as defined above;

(2) reacting a compound of formula 3 with a chiral primary amine of the formula

wherein $R^3NH_2$ is a chiral hydroxy substituted alkylamine, a chiral alkylamine substituted with both hydroxy and phenyl, (+)- or (−)- threo-2-amino-1-(4-nitrophenyl)-1,3-propanediol, (+)- or (−)-norepinephrine, (+)-2-amino-3-methoxy -1-phenylpropanol, L-tyrosinol, and lower alkyl esters of (+)- or (−)-tyrosine and (+)- or (−)-threonine in the presence of a coupling agent selected from the group consisting of 1,3-dicyclohexylcarbodiimide and 1-(3-dimethylaminopropyl)-3-ethylcarbodiimide hydrochloride to yield a mixture of compounds having the formulae

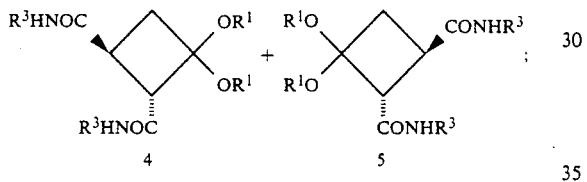

(3) separating the diastereomeric compounds of formulae 4 and 5;
(4) protecting the hydroxy groups substituted on the moiety $R^3$ in a compound of formula 4 to afford a compound having the formula

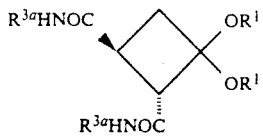                                          6 wherein the hydroxy protecting group is a hindered silyl group selected from the group consisting of t-butyldimethylsilyl, t-butyldiphenylsilyl, and triisopropylsilyl, an acyl group, an aroyl group, or trityl;

(5) reacting a compound of formula 6 with a nitrosating agent to yield a compound having the formula

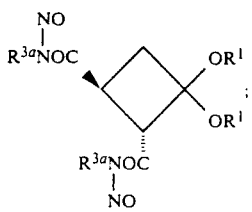                                          7

(6) treating a compound of formula 7 with a reducing agent selected from the group consisting of lithium aluminum hydride, sodium borohydride, and lithium borohydride to yield a compound of the formula

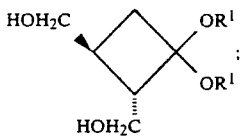                                          9

(7) reacting a compound of formula 9 with a protecting agent selected from the group consisting of t-butyldiphenylsilyl, triisopropylsilyl, benzyl, p-methoxybenzyl, acyl, and aroyl to yield a compound of the formula

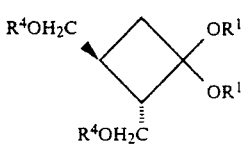                                          10 wherein $R^4$ is a protecting group and $R^1$ is as defined above;

(8) reacting a compound of formula 10 with an acid catalyst selected from the group consisting of sulfuric acid, hydrochloric acid, and p-toluenesulfonic acid to yield a compound of the formula

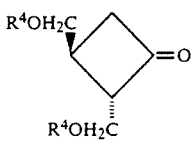                                          11 wherein $R^4$ is as defined above;

(9) reacting a compound of formula 11 with a reducing agent selected from the group consisting of lithium trisec-butylborohydride, lithium trisiamylborohydride, diisobutylaluminum hydride, dicyclohexylborane, and disiamylborane to yield a compound of the formula

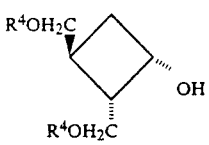                                          12 wherein $R^4$ is as defined above;

(10) reacting a compound of formula 12 with a sulfonylating reagent to yield a compound of the formula

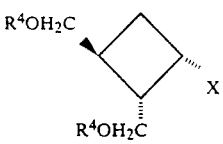                                         13 wherein X is an alkanesulfonyloxy group, a substituted alkanesulfonyloxy group, an arenesulfonyloxy group, or a substituted arenesulfonyloxy group and the sulfonylating reagent is the corresponding sulfonic anhydride or sulfonyl chloride;

(11) reacting a compound of formula 13 with guanine or a protected guanine to yield a compound of the formula

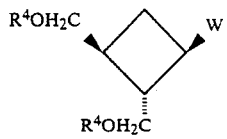

14 wherein W is a 9-guanyl residue or a protected 9-guanyl residue and $R^4$ is as defined above; and

(12) deprotecting a compound of formula 14 to yield the compound of formula 1.

2. A process according to claim 1 wherein the chiral primary amine is a chiral alkylamine substituted with both hydroxy and phenyl.

3. A process according to claim 2 wherein the chiral alkylamine is R-(−)-2-phenylglycinol.

4. A process according to claim 1 wherein $R^1$ and $R^2$ are each ethyl.

5. A process according to claim 1 wherein the hydroxy protecting group in step (4) is t-butyldimethylsilyl.

6. A process according to claim 1 wherein the nitrosating agent in step (5) is nitrogen tetroxide.

7. A process according to claim 1 wherein the reducing agent in step (6) is lithium borohydride.

8. A process according to claim 1 wherein the compound of formula 9 is treated with benzoyl chloride in step (7) to give the compound of formula 10 wherein $R^4$ is benzoyl.

9. A process according to claim 1 wherein the acid catalyst in step (8) is sulfuric acid.

10. A process according to claim 1 wherein the reducing agent in step (9) is lithium trisiamylborohydride.

11. A process according to claim 1 wherein the sulfonylating agent in step (10) is p-toluenesulfonyl chloride.

12. A process according to claim 1 wherein the guanine employed in step (11) is 2-amino-6-benzyloxypurine.

13. A process according to claim 1 wherein:
a) $R^1$ and $R^2$ are ethyl;
b) the chiral alkylamine in step (2) is R-(−)-2-phenylglycinol;
c) the hydroxy protecting group in step (4) is t-butyldimethylsilyl;
d) the nitrosating agent in step (5) is nitrogen tetroxide;
e) the reducing agent in step (6) is lithium borohydride;
f) the protecting reagent employed in step (7) is benzoyl chloride;
g) the acid catalyst in step (8) is sulfuric acid;
h) the reducing agent in step (9) is lithium trisiamylborohydride;
i) the sulfonylating agent in step (10) is p-toluenesulfonyl chloride;
j) the guanine employed in step (11) is 2-amino-6-benzyloxypurine; and
k) the benzoyl $R^4$ protecting group is removed by basic hydrolysis and the guanine is deprotected by acid hydrolysis.

14. A process for the preparation of the optically active compound [1R-(1α,2β,3α)]-2-amino-9-[2,3-bis(-hydroxymethyl) cyclobutyl]-1,9-dihydro-6H-purin-6-one, represented by the formula

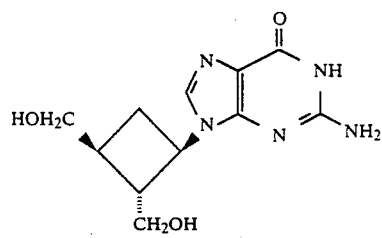

1 which comprises
(1) reacting a racemic compound of the formula

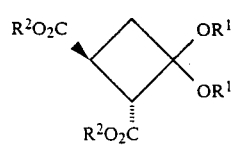

2 wherein $R^1$ and $R^2$ are lower alkyl with alkali to yield the racemic compound of the formula

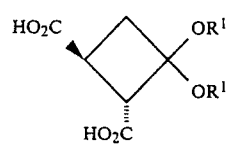

3 wherein $R^1$ is as defined above;
(2) reacting a compound of formula 3 with a chiral primary amine of the formula $R^3NH_2$ wherein $R^3NH_2$ is a chiral alkyl amine, a chiral phenyl or naphthyl-substituted alkyl amine, (+)- or (−)-α-methyl-p-nitrobenzylamine, (+)-dehydroabietylamine, or a lower alkyl ester of an α-amino acid selected from the group consisting of (+)-alanine, (−)-alanine, (+)-valine, (−)-valine, (+)-leucine, (−)-leucine, (+)-isoleucine, (−)-isoleucine, (+)-phenylalanine, (−)-phenylalanine, (+)-serine, and (−)-serine in the presence of a coupling agent selected from the group consisting of 1,3-dicyclohexylcarbodiimide and 1(3-dimethylaminopropyl)-3-ethylcarbodiimide hydrochloride to yield a mixture of compounds having the formulae

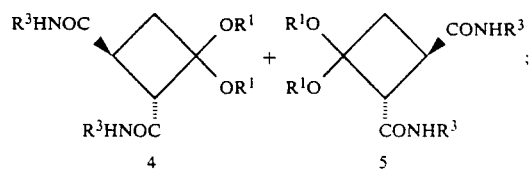

4        5

(3) separating the diastereomeric compounds of formulae 4 and 5;
(4) reacting of compound of formula 4 with a nitrosating agent to yield a compound having the formula

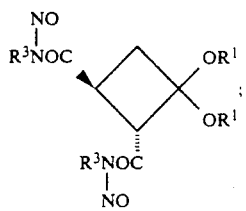

(5) treating a compound of formula 8 with a reducing agent selected from the group consisting of lithium aluminum hydride, sodium borohydride, and lithium borohydride to yield a compound of the formula

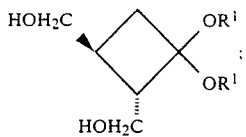

(6) reacting a compound of formula 9 with a protecting agent selected from the group consisting of t-butyldiphenylsilyl, triisopropylsilyl, benzyl, p-methoxybenzyl, acyl and aroyl to yield a compound of the formula

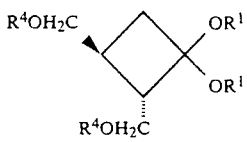

wherein $R^4$ is a protecting group and $R^1$ is as defined above;

(7) reacting a compound of formula 10 with an acid catalyst selected from the group consisting of sulfuric acid, hydrochloric acid, and p-toluenesulfonic acid to yield a compound of the formula

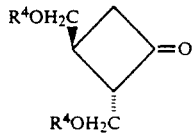

wherein $R^4$ is as defined above;

(8) reacting a compound of formula 11 with a reducing agent selected from the group consisting of lithium tri-sec-butylborohydride, lithium trisiamylborohydride, diisobutylaluminum hydride, dicyclohexylborane, and disiamylborane to yield a compound of the formula

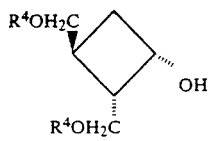

wherein $R^4$ is as defined above;

(9) reacting a compound of formula 12 with a sulfonylating reagent to yield a compound of the formula

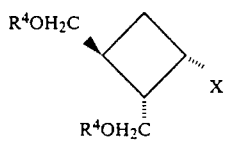

wherein X is an alkanesulfonyloxy group, a substituted alkanesulfonyloxy group, an arenesulfonyloxy group, or a substituted arenesulfonyloxy group and the sulfonylating reagent is the corresponding sulfonic anhydride or sulfonyl chloride;

(10) reacting a compound of formula 13 with guanine or a protected guanine to yield a compound of the formula

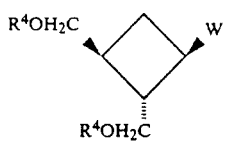

wherein W is a guanyl residue or a protected 9-guanyl residue and $R^4$ is as defined above; and

(11) deprotecting a compound of formula 14 to yield the compound of formula 1.

* * * * *